United States Patent [19]
Wurster et al.

[11] Patent Number: 5,591,186
[45] Date of Patent: Jan. 7, 1997

[54] SELF-CUTTING TROCAR

[76] Inventors: Helmut Wurster, Mozartstrasse 20, 75038 Oberderdingen; Gerd Buess, Klostermuehle 7, 72074 Tuebingen, both of Germany

[21] Appl. No.: 615,635

[22] Filed: Mar. 13, 1996

Related U.S. Application Data

[63] Continuation of Ser. No. 240,586, May 9, 1994, abandoned, which is a continuation-in-part of Ser. No. 887,151, May 22, 1992, abandoned.

[30] Foreign Application Priority Data

May 22, 1991 [DE] Germany ............... 41 16 648.5

[51] Int. Cl.$^6$ .................................. A61B 17/34
[52] U.S. Cl. ................. 606/170; 606/185; 604/164
[58] Field of Search ................. 606/185, 182, 606/172, 167, 171, 170; 604/164; 128/751

[56] References Cited

U.S. PATENT DOCUMENTS 4,985,035  1/1991  Torre ............................. 606/167
5,403,296  4/1995  Mohring et al. ............... 604/274

FOREIGN PATENT DOCUMENTS 2640490  6/1990  France ............................. 606/167

*Primary Examiner*—Michael H. Thaler
*Attorney, Agent, or Firm*—Evenson, McKeown, Edwards & Lenahan P.L.L.C.

[57] ABSTRACT

A self-cutting trocar pin is provided near its distal end with active cutting tools, operated manually or motor driven. Therefore, the force which is normally needed to insert the trocar into a body is greatly reduced, and the insertion can be done under control to avoid the risk of injury during penetration of the abdominal wall. A gas flow sensor indicates opto acoustically, in connection with an opening near the distal end of the trocar pin, the penetration of the abdominal wall. The cutting tool of the trocar pin maybe, for example, a disc shaped blade, a chain knife, or manually operated straight blades.

6 Claims, 10 Drawing Sheets

SELF-CUTTING TROCAR

This application is a continuation of application Ser. No. 08/240,586, filed on May 9, 1994, now abandoned, which was a continuation-in-part application of application Ser. No. 07/887,151, filed on May 22, 1992, which has been abandoned.

FIELD OF THE INVENTION

The present invention relates to trocars in which a trocar pin or obturator is carried by a trocar sheath (sleeve or cannula). More particularly, the invention is directed to improved trocar pins, especially the type thereof which cut with less applied force so as to avoid organ injury.

BACKGROUND OF THE INVENTION

Insertion of the trocar into the body is the presupposition for carrying out an endoscopic diagnosis or therapy in the abdomen. After penetrating the body wall with the trocar, the trocar pin is removed from the trocar sleeve, which stays in the abdominal wall, and an endoscope or endoscopic instrument is inserted through the sleeve. Before introducing the trocar, a pneumoperitoneum is established, using $CO_2$ gas, to achieve a distance between the abdominal wall and the organs. Upon inserting the trocar through the abdominal wall the sharp trocar tip may injure the organs if it penetrates too deeply by not working cautiously and carefully.

According to the state of art (FIG. 1) different shapes of trocar tips are in use. For example, conical, three-faced-pyramidal with sharp edges, and also conically threaded for screwing-in are sometimes used. To reduce risk of injury EP 0265 193 describes a protective sleeve, surrounding the trocar tip (FIG. 2). The sleeve snaps forward, shielding the sharp tip, after the trocar has penetrated the abdominal wall. For penetrating the tissue, there is still a relatively large force to be expended, and the safety mechanism does not come into play until the tip has fully entered the abdomen. The forward jumping of the sleeve only avoids injury occurring after pushing the trocar forward into deeper regions, due to the suddenly reduced resistance. Another method is described in EP 0135 364 B 1 dealing with a triple bladed knife, which moves forward out of the trocar sleeve to cut through the body wall. The trocar is pushed into the cut and then the blade is retracted into the body, the cone is pressed back by the body tissue and the blades cut. After having penetrated the body wall, the cone snaps forward and protects the blades in its slots. This method also has the disadvantage that it needs a rather high penetration or cutting force and entails the same dangers as the pyramidal trocar.

An object of the present invention is to avoid the sudden further penetration of the trocar due to the force applied by the operating surgeon, and reduce the risk of injuries after having penetrated the body wall. The force acting on the trocar has to be reduced, to avoid the sudden dangerous movement.

BRIEF SUMMARY OF THE INVENTION

The object of the invention is achieved by an active self-cutting trocar, having cutting tools which are manually moved relatively to the trocar pin, allowing cutting through the body wall using a low force for the operating surgeon to move the trocar forward. With the blade retracted, the surgeon can penetrate the trocar by dialating. This controlled insertion of the trocar has the advantage of a much lower risk of injuries, compared to the methods used up to now.

Furthermore, a gas flow sensor is able to tell the operating surgeon when the trocar tip has penetrated the body wall, by transmitting an optical and/or acoustical signal. Compared to the state of art, which up to now used mostly the pyramidal sharp-edged trocar (FIG. 1), it is advantageous and increases patient safety, when the trocar can be introduced at the lowest possible force. Thereby the "sudden forward push"—the uncontrolled forward moving of the trocar tip after the loss of the penetration resistance—is avoided.

BRIEF DESCRIPTION OF THE DRAWINGS

The foregoing summary of the invention, as well as the following detailed description of preferred embodiments, will be better understood when read in conjunction with the appended drawings. For the purpose of illustrating the invention, there are shown in the drawings embodiments which are presently preferred, it being understood, however, that the invention is not limited to the specific arrangement and instrumentalities disclosed.

DETAILED DESCRIPTION OF PREFERRED EMBODIMENTS

Figure 1:
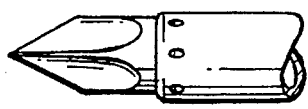
FIG. 1 is a plan view of the distal end of a pyramidal type trocar of the prior art having sharp edges.
Figure 2:
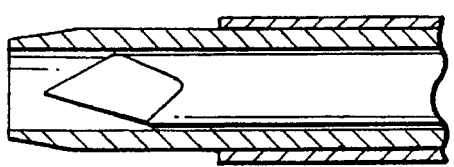
FIG. 2 is a partial cross-sectional view of the distal end of a pyramidal trocar of the prior art with automatic protection shield.
Figure 3:
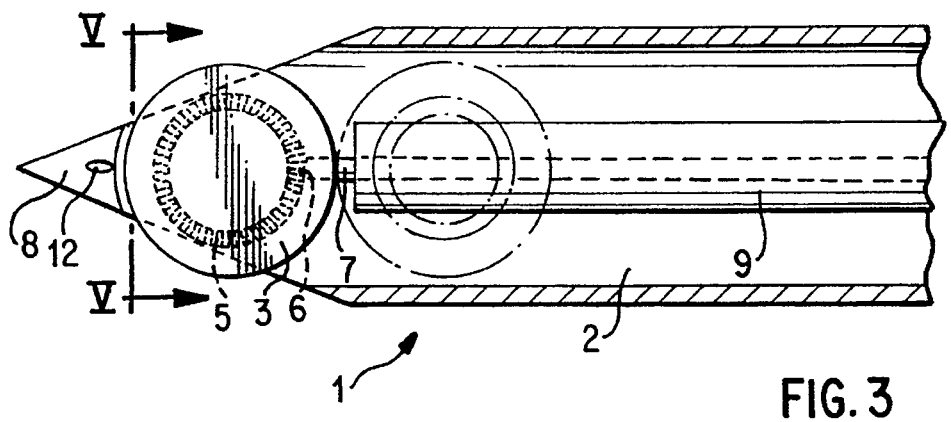
FIG. 3 is a partial cross-sectional plan view of the distal end of an active cutting trocar with an electrically driven cutting disc, according to one embodiment of the invention.
Figure 4:
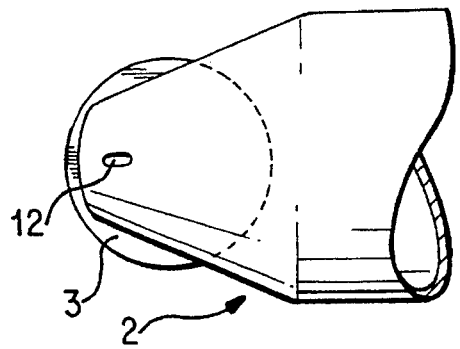
FIG. 4 is a plan view of the head of a trocar pin as in FIG. 3, but without the pointed trocar tip.
Figure 5:
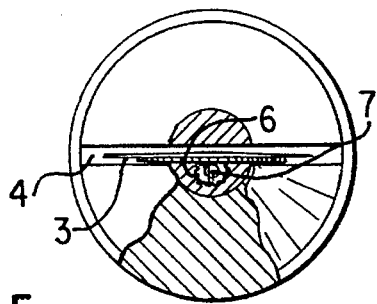
FIG. 5 is a distal end view of the trocar of FIG. 3 taken along line III—III, and partially broken away in section to show the details of the drive system.

The cutting effect of the trocar in a first embodiment is achieved by a cold cutting blade, which is rotated. The tissue is separated actively, the opening enlarged and the trocar guided forward into this opening. This is a controlled movement, for which only a low force is needed and which is therefore precisely done and controlled by the operating surgeon. FIGS. 3, 4 and 5 show this first embodiment of this invention.

The trocar 1 with its shaft or pin 2 is shaped conically at its distal end. The conical part contains a rotating cutting disc 3, positioned in a slot 4, motor driven by a toothed rim 5, a gear wheel 6 and drive axle 7. For inserting the trocar, tip 8 is positioned in an incision made with a surgical knife, and then the rotating blade takes over the cutting function, and the trocar slides easily (self-cutting) through the body wall.

To optimize the cutting performance, e.g. as for the forceless insertion of the trocar, a modification of the diameter of the knife and the position of the knife axle may be useful. A modified embodiment is shown in FIG. 4, where the pointed tip 8 is omitted. This trocar cuts at its front end also, and because of the easier insertion, the incision by the surgical knife is no longer needed.

Figure 6:
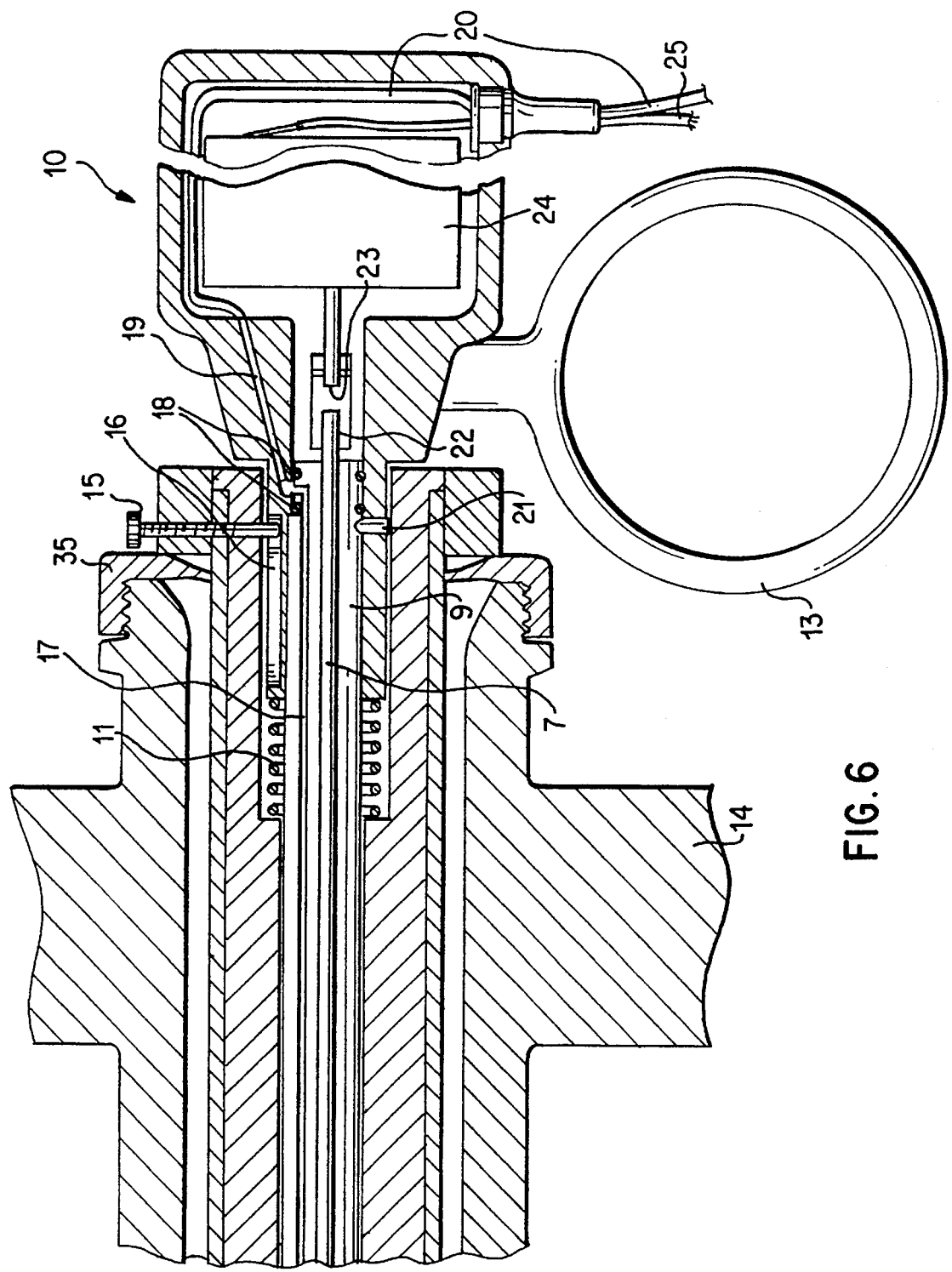
FIG. 6 is a cross-sectional view of the proximal end of the trocar of FIG. 3, showing the attached drive system and gas supply.

For protecting the knife and also for protecting against unwanted cutting, knife 3 with its drive (5,6,7) is mounted on carrier 9, to which the drive unit 10 (FIG. 6) is coupled. Spring 11 urges carrier 9 and the drive unit toward the proximal end so that the disc knife disappears totally into slot 4 of the trocar pin, as shown by dotted lines in FIG. 3. The shifting of carrier 9 in the trocar shaft 2 is shown in FIGS. 3 and 6. FIG. 6 shows the proximal part of the trocar and drive unit 10 coupled to carrier 9. Screw 21 fixes the parts 9 and 10 together. Part 10 is removed by loosening this screw. The splined part 22 of axle 7 is moved by clutch 23, attached to the axle of the motor 24. The gas channel 17, ending distally at opening 12 and passing proximally through the seal 18 into channel 19, is also separated. The handle 13 allows the forward movement of the knife unit, whereby e.g., the trumpet valve 14 of the trocar sleeve acts as counter handle. The movement of the knife unit on carrier 9 and motor unit 10 takes place against the force of the bias spring 11. Screw 15 and groove 16 limit the travel by a method well known by one skilled in the art.

The gas channel 17 passes into the motor housing through seal 18 into channel 19 and through tube 20, which together with the electrical motor supply cable 25, is led out to the gas flow sensor and the motor supply unit. A switch (not shown), coupled to the handle 13, starts the motor by moving the handle forward. The motor could also be started by a foot switch. Only when the operating surgeon moves the handle 13 forward is the knife brought into its cutting position.

Information about when the abdominal wall is penetrated is given to the gas flow sensor 60 (FIG. 7) through channel 17, which ends at trocar tip 8 or laterally from knife 3 at opening 12. This channel is charged through gas supply tube 20 with a gas pressure $P_1$ ($CO_2$ gas), which is about 2–8 mm Hg higher than the pressure established in the body. As long as opening 12 is covered with tissue, as during insertion, practically no gas will flow. If the opening becomes free, when the trocar tip has penetrated into the body cavity, a gas stream will flow, whose magnitude will depend on the pressure difference and the choke of the sensor 60. The change of the gas flow is sensed by the sensor 54, is processed and activates an optical and/or acoustical signal for the operating surgeon.

Figure 7:
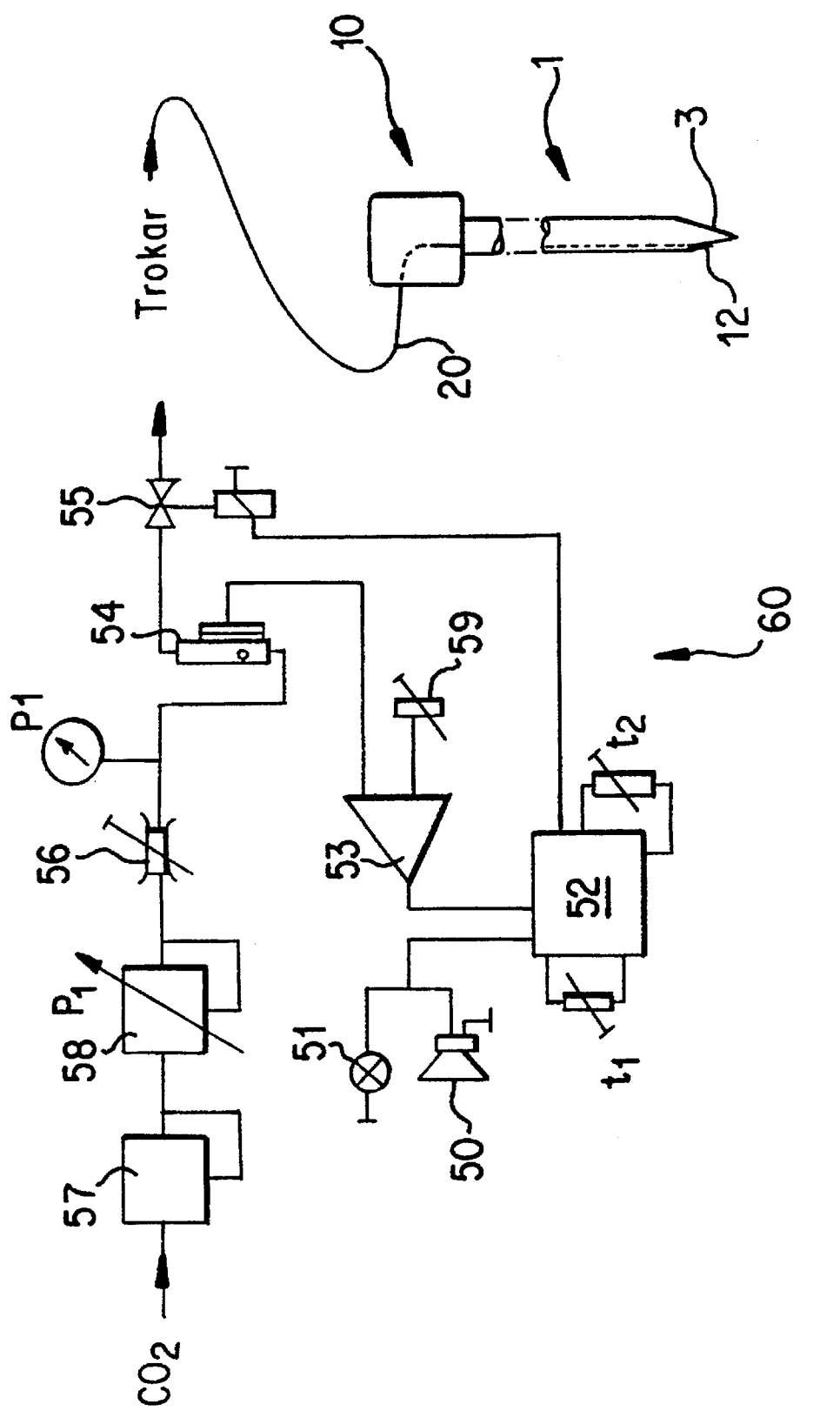
FIG. 7 is a block diagram of the gas flow sensor for opto-acoustical indication of the trocar penetration of the abdominal wall.

The gas flow sensor 60 with its processing circuit is shown in FIG. 7. In accordance with the invention this unit is advantageously designed in such a way that the gas flow is shut off automatically within an adjustable time $t_2$ (several seconds) after the signal is given. Also, the signal is only given when the gas flow is constant over a certain time $t_1$, to be sure that the trocar has completely penetrated into the body cavity. The $CO_2$ gas, taken from a gas cylinder or cartridge (not shown), is reduced in pressure by a pressure regulator 57 and brought to pressure $P_1$ by an adjustable regulator 58. Choke 56 limits the gas to the desired maximum flow. Flow meter with sensor 54 gives an electrical signal to a difference amplifier 53, whose level is adjusted by resistor 59. If the gas flow is higher than this level, the double timer 52 is activated which then activates the signal generators 50 ($t_1$) and/or 51 as well as the valve 55 ($t_2$).

FIG. 5 shows a partial cross-section through the distal end of shown in FIG. 3. The drive mechanism of the knife is additionally detailed there.

Figure 8:
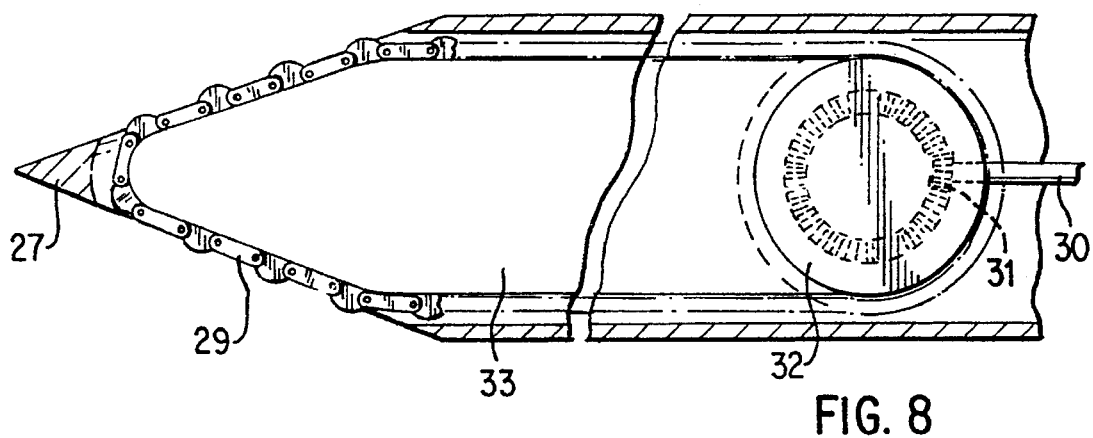
FIG. 8 is a partial cross-sectional view of the distal end of a trocar with a circular chain knife as the cutting tool.

Another embodiment example of a trocar of the invention is the replacement of the rotating knife 3 by a cutting chain 29, as shown in FIG. 8. The advantage of this is that the form of cutting line by the chain could be partially freely selected, e.g., along the conical boundary of the trocar tip.

Figure 9A:
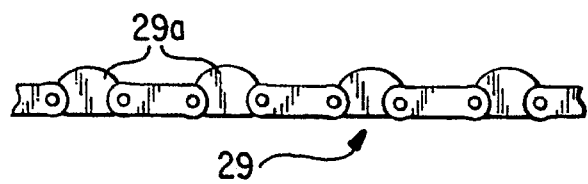
FIGS. 9A and 9B are side and top views of several links of the chain knife of FIG. 8.
Figure 9B:
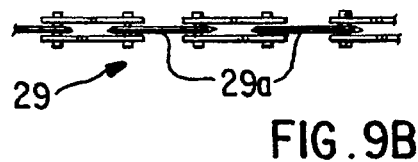

Chain 29 has a minimal bending radius, depending upon the length of the chain link. Small radii can be realized if a fine-linked chain is used. The chain is constructed in such a way that between two chain links another chain link with a knife 29a is placed. FIGS. 9A and 9B show an example of the chain.

Just as in the case of the trocar with the disc knife, the tip of the chain cutting trocar could be left off analogous to FIG. 4, so that the knife then cuts around the tip.

The drive of the chain is located toward the proximal part of the trocar in which the chain wheel 32 is driven by an electrical motor drive unit 10, such as shown in FIG. 6. The chain embodiment consists of a gear wheel 31, axle 30, chain wheel 32, forming a unit 33 which can be moved backward together with the drive unit so that the chain 29 is inside of the trocar tip boundary and no tissue is cut. In this rest position, which is maintained by a spring (not shown in FIG. 8), the trocar pin is inserted into the trocar sleeve. This avoids, just as in cases of the other self-cutting trocars of the invention, damage to the sealing cap 35 (FIG. 6) of the trocar sleeve, which occurs during insertion of the pyramidal ones, which are in use now. A damaged sealing cap for the trocar sleeve leads to continuous gas loss from the abdomen, during the endoscopic procedure, which must be compensated for.

Figure 10:
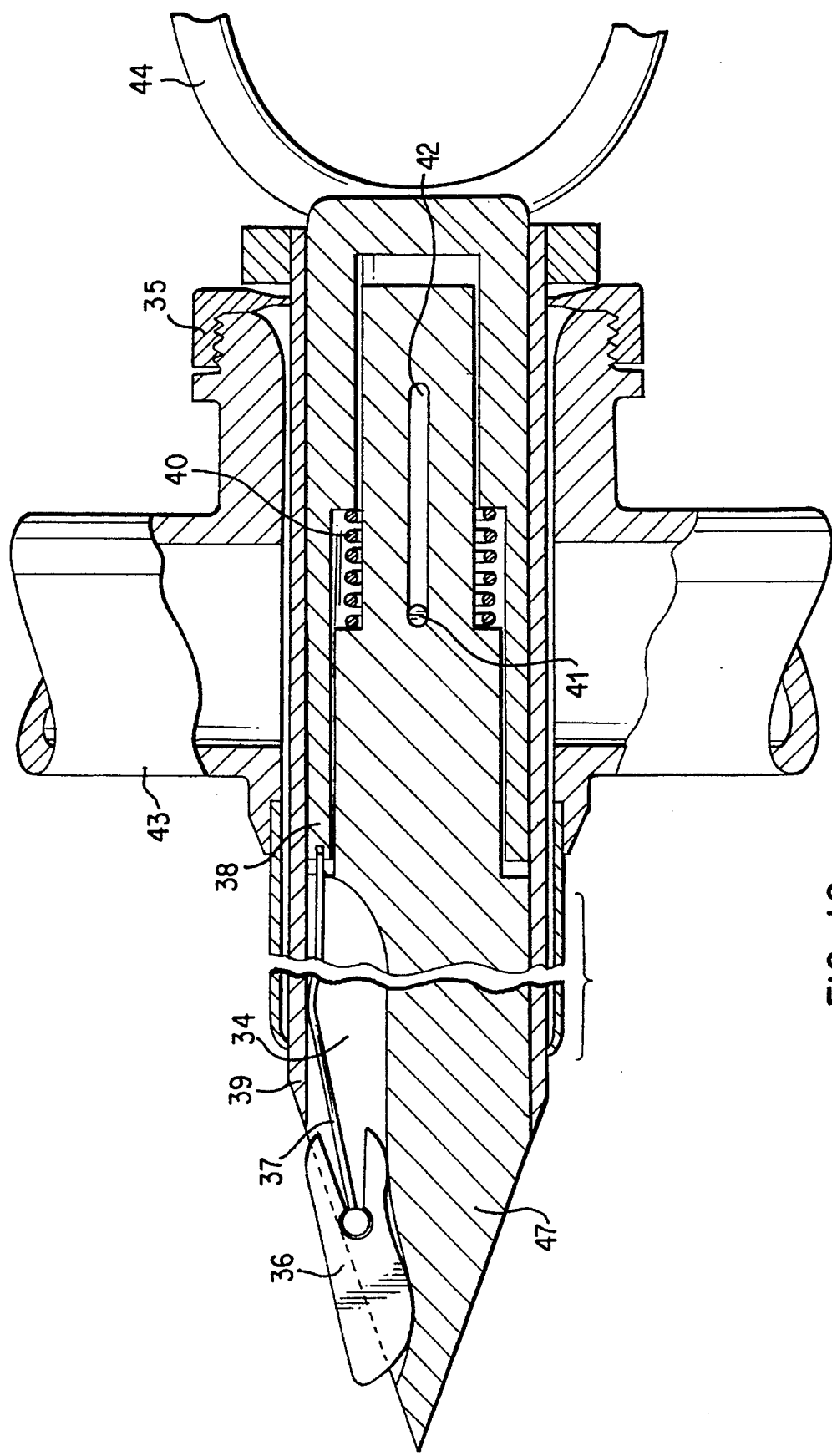
FIG. 10 is a partial cross-sectional view of an active cutting trocar with manually activated blades.

The motor unit for the drive could for this embodiment also be attached at a right angle to the trocar and would then lie in the axis of the chain wheel 32. This motor unit is also detachably arranged and can be used as a handle during insertion of the trocar. In this embodiment of the invention the use of an opening 12 for indication of penetration of the body wall is also possible, as explained before and shown in FIG. 7. A further embodiment according to the invention is shown in FIG. 10. One or more symmetrically arranged lengthwise slots 34 around the trocar pin 47 are used to guide knife blades 36, which are connected mechanically by the connecting bars 37 to the actuation tube 38. The connecting bar 37 has the function of operating the blade longitudinally in the slot and has a spring function, so that the blade is biased toward the bottom of the slot, for which connecting bar is so shaped that it presses against the outer sleeve 39. By pushing the tube 38 against the force of the spring 40, the blades slide in the slots 34 and move out of the conical part of the trocar tip with their cutting edges, to perform a cut into the tissue. To operate the blades, the trocar is held by two fingers at the counter handle 43 (trumpet valve) of the trocar sleeve and moved forward by the thumb, located in the ring handle 44. Pushing forward the handle 44, the actuation tube 38 moves the blades forward by means of the connecting bars, out of their rest position along the slots in the conical part of the trocar. The tissue is thereby cut and the trocar tip slides along this cut deeper into the body wall. By multiple actuation of the blades the abdominal wall is finally penetrated. In this embodiment of the invention, the above-mentioned gas flow sensor and opening 12 (not shown in FIG. 10) could also be used.

The limitation of movement is accomplished by a slot 42 into the trocar pin 47 and by a pin 41 connected to the actuation tube. The trocar is also inserted into the trocar sleeve with blades pulled back (rest position) into the outer sleeve 39 of the trocar pin so that the seal 35 will not be damaged.

Figure 11:
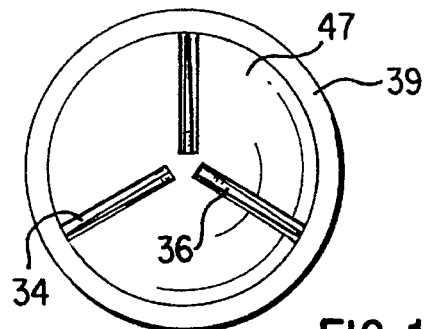
FIG. 11 is a distal end view of the trocar of FIG. 10 with extended blades.
Figure 12:
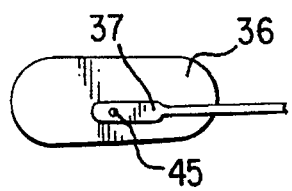
FIG. 12 is a detail view of a blade connection similar to that of the embodiment of FIGS. 10 and 11.
Figure 13:
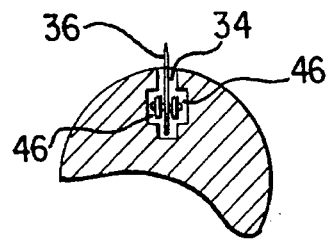
FIG. 13 is a cross-sectional view of a blade guide with lateral grooves for the blade connection of FIG. 12.

A further modification of the blade guiding is possible when the blade 36 has a pin 45 which forms the connection to the connecting bar 37, as shown in FIG. 12. For this, the slot 34 must have lateral grooves 46 in the walls of the slot as shown in FIG. 13. In this case the spring function of the connection bar, which urges the blades to the bottom of the slot, is not needed. The connection bar need only be bendable in order to follow the contour of the cone. The end view of an advantageous embodiment with three blades is shown in FIG. 11, which corresponds in function to the current pyramidal trocar, but having the additional advantages of the present invention.

Figure 14:
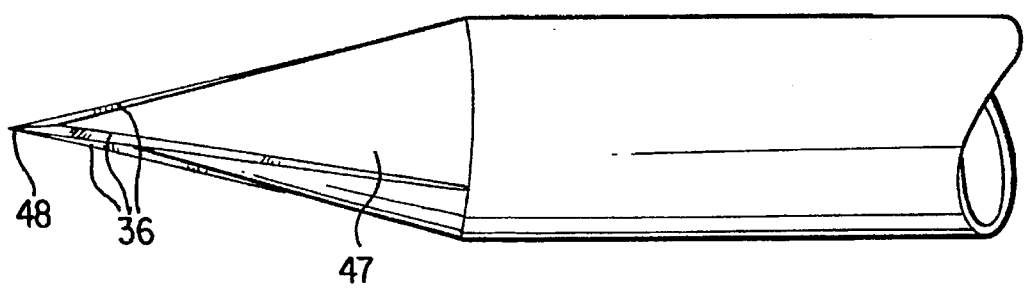
FIG. 14 is a perspective view of the distal end of a trocar pin according to another embodiment with blades in their forward (extended) position.
Figure 15:
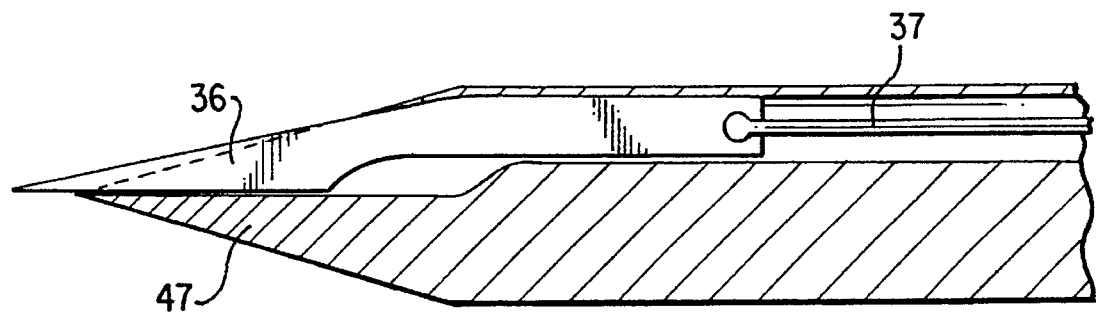
FIG. 15 is a partial cross-sectional view of the trocar tip of FIG. 14 showing a blade in its extended position.

A further embodiment of the invention is shown in FIGS. 14 and 15, similar to the embodiment of FIGS. 10 and 11, but where three knife blades 36 together form a unitary cutting tip 48. The tip of the head 49 can be blunt, for not making injuries after penetration with retracted blades. This feature allows the dilating penetration of the body wall without using the knife blades, which is the preferred method by the surgeons. If the dilating goes too strong, the knife blades can be operated to make incisions for easier penetration when needed. The ratio between dilating and cutting is determined by the surgeon and can be adapted to the tissue of the patient. In a modification (not shown) of the embodiment, the trocar pin 47 could have only two slots instead of three, and the knife could be formed as one blade with two cutting edges (FIG. 18).

Figure 16:
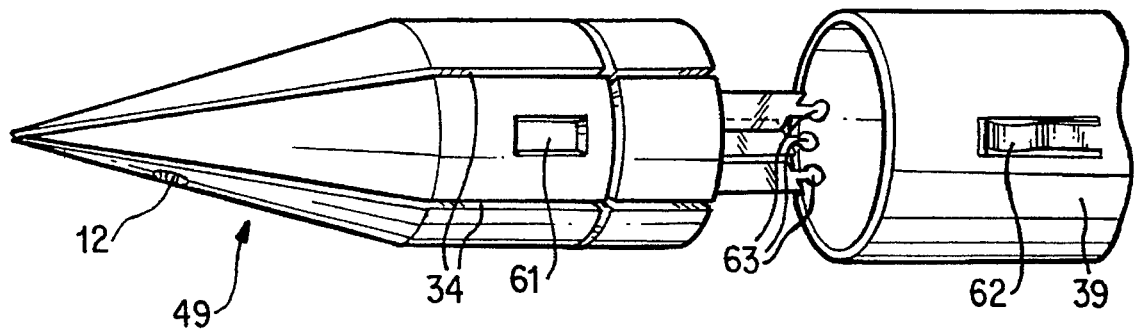
FIG. 16 is an exploded perspective view of another trocar according to the invention and having a disposable head.

Still another embodiment of the invention is shown in FIG. 16, where the tip or head 49 of the trocar pin with the knife blades therein (such as the blades of FIGS. 10 and 11 or FIGS. 14 and 15) could be pulled out of the trocar pin and be disposable. The advantage of this embodiment is an inexpensive trocar system with a sharp set of blades for each patient. In this embodiment the disposable head 49 slips into the outer sleeve 39 and snaps into place by means of a conventional aperture 61 and detente 62 arrangement. Similarly, the proximal ends 63 of the blades can snap into connecting bars or directly into the actuation tube (not shown) inside outer sleeve 39.

Figure 17:
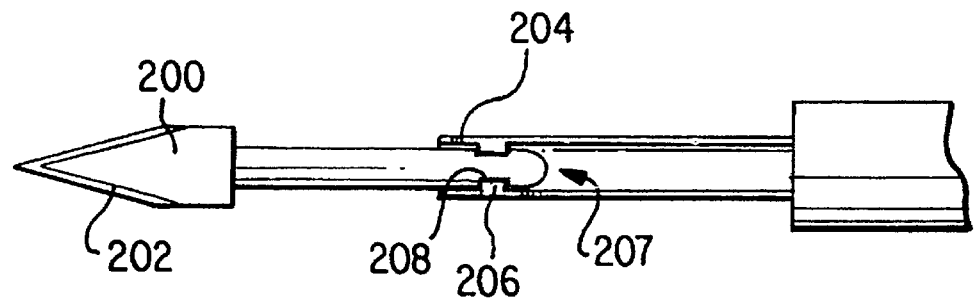
FIG. 17 is a detail of an embodiment according to the present invention of a detachable connection of the blade.

In certain embodiments of the present invention, an arrangement is provided to make the blade readily detachable. In FIG. 17, a blade 200 is shown having cutting edges 202, and a connection head 207. The connection head 207 has recesses 208 into which connection bar hooks 206 of the connection bars 204 engage. The connection bars 204 are springy in nature.

Figure 18:
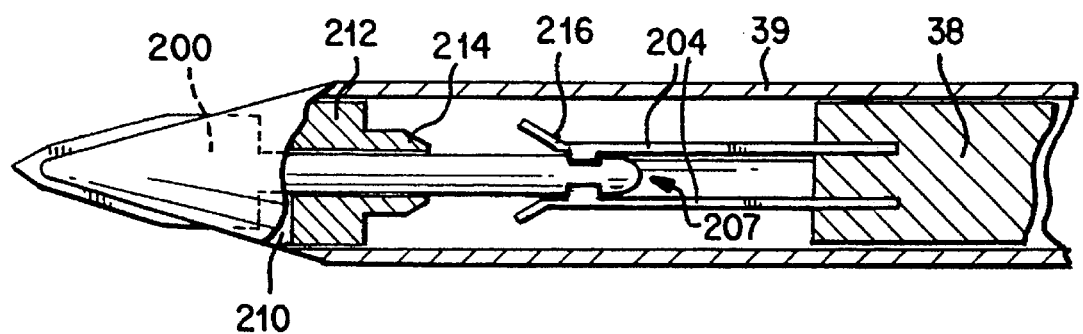
FIG. 18 shows the embodiment of FIG. 17 illustrating the detaching operation of the blade.

FIG. 18 shows how the detaching of the blade 200 is accomplished. The pin 212 of the trocar has ramps 214 onto which angled ends 216 slide to open the connection bars 204 and disengage the connection bar hooks 206 from the recesses 208 of the connection head 207. This position in which the angled ends 216 contact the ramps 214 is well forward of the normal activated position of the blade 200 (shown extending out of the slot 210 in FIG. 18). The embodiment of FIGS. 17 and 18 can be used with the other blade embodiments of the present invention.

Figure 19:
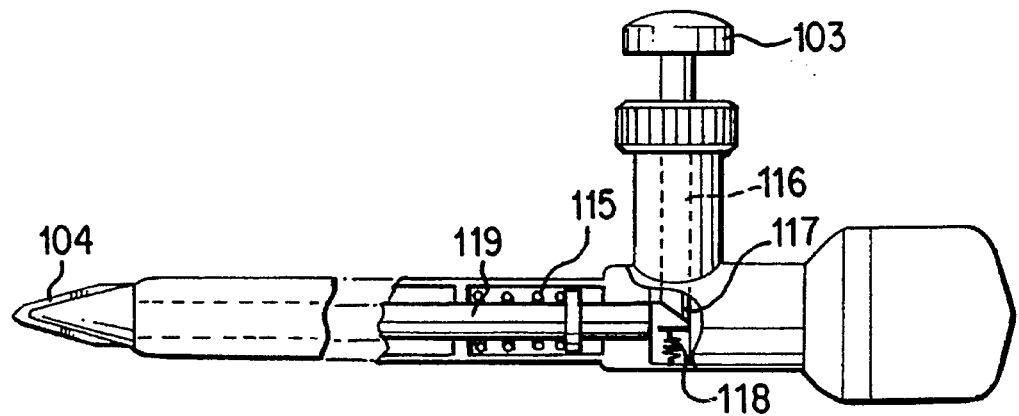
FIG. 19 shows an embodiment of the trocar of the present invention.
Figure 20:
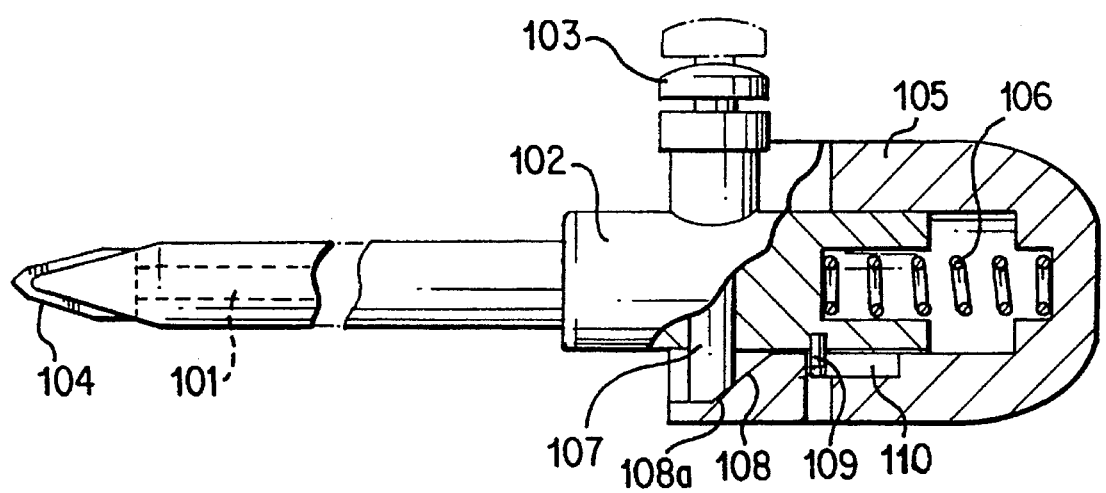
FIG. 20 shows another embodiment of the trocar of the present invention similar to the embodiment of FIG. 19, but with an additional safety feature.

FIG. 19 shows an embodiment that uses the detachable blade of FIGS. 17 and 18 which has an activation mechanism for placing the blade in an activation position. The trocar has a knob 103 with a pin 116 having a wedge 117 at the end of the pin 116. This knob is pressed downwardly against the force of a spring 118 (schematically illustrated in FIG. 19). The wedge 117 presses against the operating bar 119 connected to the blade 104 by the connection bars 204. This presses the operating bar 119 forward against a second spring 115. The cutting edges and the tip of the blade are outside of the blunt cone of the trocar pin for cutting (FIG. 20). Release of the knob 103 causes the blade operating bar 119 to move the blade 104 back into the cone of the trocar so that it is no longer in an active cutting position.

The embodiment of FIG. 19 provides the advantage that a surgeon can use the trocar for cutting when the blade is in the active cutting position and with a retracted blade can dialate the tissue by pressing the trocar into the tissue and rotating it back and forth. This method is preferable to surgeons when cutting the body wall fully through will make less compression than by dilation, if there will only be small bleeding.

The embodiment of FIG. 20 has an additional safety feature to prevent a surgeon from accidentally punching through a body wall with the blade out under high force. The activation of the blade is the same as that shown in the embodiment of FIG. 19. However, this embodiment prevents dilation with the blade out. This is accomplished by ensuring that cutting can only be done when there is a small force on the trocar handle, and that without the blade activated, maximum force can be applied with the trocar to provide dilation.

This is achieved by the provision of a handle 105 that is movable relative to the trocar pin 101 against the force of a spring 106. The handle 105 has a wedge 108, while the pin 107 of the knob 103 has a second wedge 108a, in addition to the wedge 117 that operates the operating bar 119. The wedge 108 of the handle 105 slides on the oblique end (the wedge 108a) of the pin 107. If a force is applied on the handle 105, the handle is moved against the trocar, pressing on the spring 106 so that the wedge 108 pushes the pin 107 upwards to cause the operating bar 119 to move the blade 104 to a deactivated position. A screw 109 engageable in a groove 110 is used to limit the travel of the handle 105.

By the above-described features, the trocar can only be pressed in with a large force into a body wall (dialating operation) when the blade is deactivated. If a surgeon has activated the blade and starts pressing with excessive force, the blade will move into the deactivated position to allow dialation. If further proceeding with dialation cannot be done, the surgeon can release the pressure from the handle 105 and operate the blade 104, but only under low force. This prevents the surgeon from punching through a body wall with an activated blade and pushing further into the interior of a body and cause injury to the inner organs. In the illustrated embodiment, the tip of the trocar is blunt so that no injuries will occur, even when the surgeon pushes against inner organs.

Figure 21:
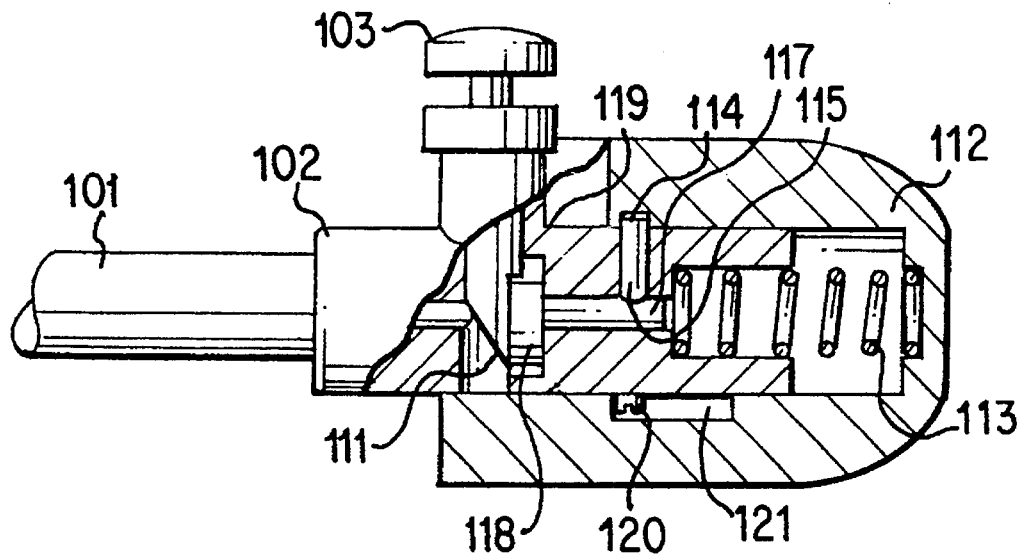
FIG. 21 shows another embodiment of the trocar of the present invention similar to the embodiment of FIG. 20, but with a different embodiment of the additional safety feature.
Figure 22:
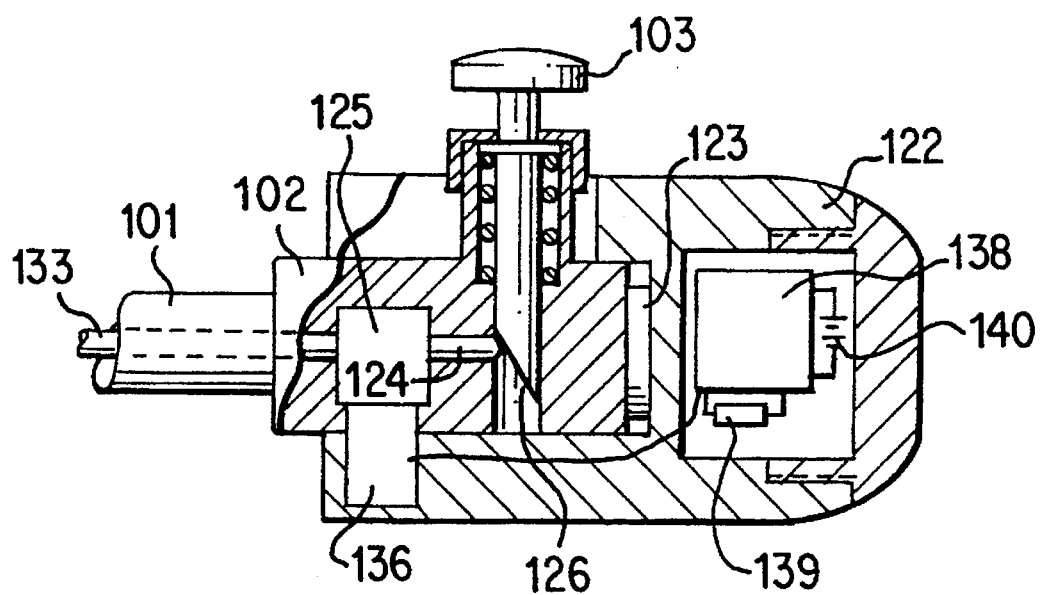
FIG. 22 shows another embodiment of the trocar of the present invention similar to the embodiment of FIG. 20, but with a still different embodiment of the additional safety feature.

The embodiment of FIG. 21 includes a spring groove 114, which is a steep thread. When the handle 112 is pressed against the force of spring 113, the spring groove 114 is moved. Pin 115 is engaged in the thread of the spring groove 114. The pin 115, connected to an axle 117, causes the axle 117 to rotate when the spring groove 114 is moved. Eccentric 118 is turned by the axle 117 to move the operating knob 103 upwardly and the operating bar is moved via wedge 111, so that the blade is placed into a deactivated position. In this embodiment also, a screw 120 and a groove 121 are provided for limiting the travel of handle 112. This embodiment thus provides a different arrangement but the same function as the embodiment of FIG. 20.

The same functionality is also provided by the embodiment of FIGS. 22–25. In this embodiment, the spring 113 is replaced by a force sensor 123. (The blade operation mechanism is the same as that shown in FIGS. 19–21.) Knob 103 is pressed down and the wedge 126 pushes the blade operating bar 124 connected through element 125 to the blade operating bar 133 forward. Element 125 is an electromagnetically operated disconnecting unit that couples and decouples the bars 124 and 133. The force sensor 123 is connected to a circuit 138 coupled to a battery 140. When the force on the handle 122 exceeds a level set by potentiometer 139, a signal is provided from the force sensor 123. An electrical signal at the output of circuit 38 activates the electromagnet 136 of element 125. The transmission of the blade operating bar 133, 124 is then disconnected and knob 103 is disfunctional.

Figure 23:
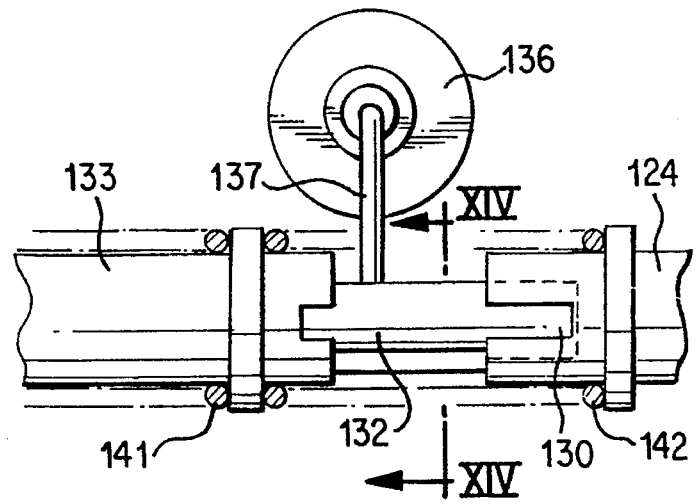
FIG. 23 shows a detail of the electromagnetic system used in the embodiment of FIG. 22.
Figure 24:
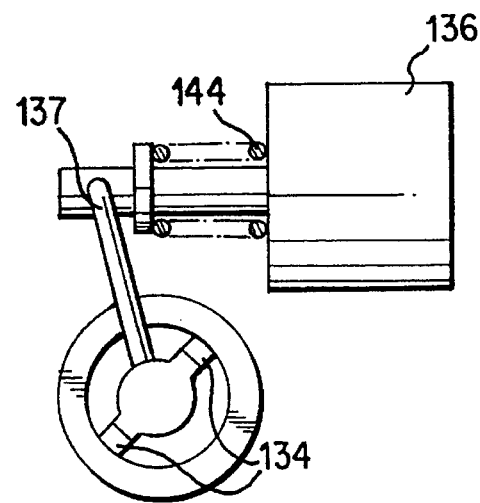
FIG. 24 is a section along line A—A of FIG. 23.

Element 125 is shown in more detail in FIG. 23, in which element 132 has wedges 134 (FIG. 24) which span the distance between bars 124 and 133. If element 132 is rotated by the electromagnet 136 over the lever 137, the wedges 134 move into the grooves 130. The operating bar for the blade is thereby shortened and the blade is retracted by spring 141, so that the wedge 126 cannot further operate the bar 124. When the force from the handle 122 is removed, the force sensor 123 will provide a signal and the amplifier circuit 138 will switch off the voltage to the electromagnet 136. The wedge part 132 is rotated back and the operating bar 124, 133 becomes full length and is operable again by the knob 103. To save battery energy, the electromagnet can be made in a bistable version. The circuit 138 then provides a positve (above the force level) and a negative (going below the force level) pulse, which will switch the electromagnet into its predetermined position.

Figure 25:
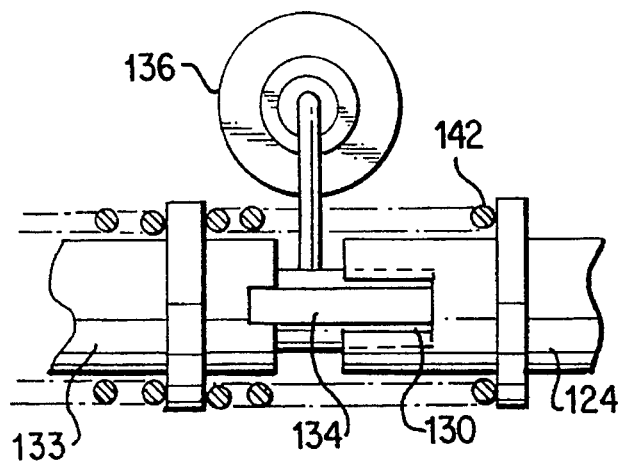
FIG. 25 is a view of the detail of the electromagnetic system shown in FIG. 23, but in a different position.

FIG. 25 shows the wedges 134 within the groove 130. A spring 142 presses bars 133, 124 apart so that wedge part 132 can rotate back when the voltage from the electromagnet 136 is released. Spring 142 is much weaker than spring 141. The spring 144 is used to move the magnet into its rest position, as well as wedge part 132.

The present invention may be embodied in other specific forms without departing from the spirit or essential attributes thereof and, accordingly, reference should be made to the appended claims, rather than to the foregoing specification as indicating the scope of the invention.

What is claimed is:

1. A self-cutting trocar pin for use in a trocar sleeve for penetrating a body wall of a patient, said trocar pin being hollow and having a longitudinal axis, a distal end and a proximal end, said proximal end having a handle and said distal end being tapered and having at least one cutting tool therein movable relative to the trocar pin toward and away from an active cutting position, said at least one cutting tool having at least one cutting edge forming cutting surfaces directed radially outwardly at a non-perpendicular angle from said longitudinal axis, an actuating device having a first means on the trocar pin for moving the at least one cutting tool relative to the trocar pin along the longitudinal axis, so as to move the cutting surfaces toward and away from the active cutting position and a second means movable relative to the first means so as to automatically move the cutting surfaces away from the active cutting position when a distally directed pressing force on the handle exceeds a predetermined value, whereby movement of said cutting tool toward the distal end places said cutting tool in the active cutting position in which the cutting surfaces extend laterally out of the tapered distal end of said trocar pin and movement of said cutting tool toward the proximal end places said cutting tool in a non-cutting position in which the cutting surfaces are within the tapered distal end.

2. A self-cutting trocar pin in accordance with claim 1, wherein said cutting tool comprises at least one blade, guidable in a diametral slot at the tapered distal end, wherein the blade has a tapered shape which forms the cutting edges, a connection bar coupled to the blade by which the blade is movable longitudinally, and a spring-loaded hook which detachably couples the connection bar to the blade.

3. A self-cutting trocar pin according to claim 1, wherein the cutting tool is located in a disposable head at the distal end of the pin, said disposable head having snap-on means for attaching and detaching said head to said pin.

4. A trocar according to claim 1, wherein the trocar pin has a spring which prestresses the handle, the handle acting against the spring when there exists a pressing force above the predetermined value, to move the handle relative to the trocar pin and via a thread-shaped groove, rotates a shaft which actuates an eccentric which presses the actuating knob into a starting position to thereby withdraw the blade.

5. A trocar comprising:

a sleeve having a conical tip area, a cutting tool in the conical tip area having at least one cutting blade and movable relative to the sleeve toward and away from an active cutting position, an actuating device having a first means actuatable to move the cutting tool relative to the sleeve in a longitudinal direction thereof distally into the active cutting position and away from the active position and a second means to disactuate the first means and move the cutting tool proximally into a non-cutting inoperative position such that the at least one blade is moved toward the active cutting position when the first means is engaged and is automatically moved away from the active cutting position when a distally directed pressing force on the trocar exceeds a predetermined value.

6. A trocar according to claim 5, wherein the second means comprises a handle and a spring which prestresses the handle, and the first means includes an actuating knob, the handle being configured and arranged to act against the spring when the pressing force is above the predetermined value and to move the handle relative to the trocar and via an oblique plane to return the actuating knob to a position in which the at least one blade is withdrawn.

* * * * *